United States Patent [19]

Vallee et al.

[11] Patent Number: 4,721,672

[45] Date of Patent: Jan. 26, 1988

[54] CDNA AND GENE FOR HUMAN ANGIOGENIN (ANGIOGENESIS FACTOR) AND METHODS OF EXPRESSION

[75] Inventors: Bert L. Vallee, Brookline, Mass.; Kotoku Kurachi, Seattle, Wash.

[73] Assignee: President and Fellows of Harvard College, Cambridge, Mass.

[21] Appl. No.: 798,547

[22] Filed: Sep. 20, 1985

Related U.S. Application Data

[63] Continuation-in-part of Ser. No. 770,657, Aug. 28, 1985.

[51] Int. Cl.$^4$ .................. C12P 21/02; C12N 15/00; C12N 5/00; C07H 15/12; H61K 37/02
[52] U.S. Cl. .................... 435/70; 435/172.3; 435/255; 435/320 R; 536/27; 935/11; 935/13; 514/12
[58] Field of Search ............ 435/91, 172.3, 317, 435/243, 253; 935/29

[56] References Cited

U.S. PATENT DOCUMENTS

| | | | |
|---|---|---|---|
| 4,229,531 | 10/1980 | Tolbert | 435/41 |
| 4,438,032 | 3/1984 | Golde et al. | 260/112 R |
| 4,503,038 | 3/1985 | Banda et al. | 424/95 |
| 4,529,590 | 7/1985 | LeVeen et al. | 424/95 |

OTHER PUBLICATIONS

Tsulsomoto et al., Cancer Res., 39:1305–1309, 1979, (Apr.).
Folkman et al., J. Exp. Med., vol. 133, 275–288, (1971).
Tuan et al., Biochemistry, vol. 12, 3159–3156, (1973).
McAuslan et al., Exp. Cell. Res., vol. 119, 181–190, (1979).
McAuslan, Control Mechanisms in Animal Cells (Jiminez de Asua, L., Shields, R., Levi-Montalcini, R., & Iacobello, S., Eds.), pp. 285–292.
Fenselau et al., J. Biol. Chem., vol. 256, 9605–9611, (1981).
Vallee et al., Experientia, vol. 41, 1–15, (1985).
Phillips et al., Int. J. Cancer, vol. 23, 82–88, (1979).
Weiss et al., Br. J. Cancer, vol. 40, 493–496, (1979).
Kumer et al., Int. J. Cancer, vol. 32, 461–464, (1983).
Shing et al., Science, vol. 223, 1296–1299, (1984).
Banda et al., Proc. Nat'l. Acad. Sci., 79:7773–7777, (1982).
D'Amore, Proc. Nat'l. Acad. Sci., 78:3068–3072.

*Primary Examiner*—Alvin E. Tanenholtz
*Assistant Examiner*—Thomas D. Mays

[57] ABSTRACT

DNA sequences encoding a protein having angiogenic activity are disclosed. Expression vectors containing these sequences are introduced into host cells and direct the production of the angiogenic protein. Proteins produced according to the invention are useful in the diagnosis of malignancies, for promoting wound healing, and for other diagnositic and therapeutic purposes.

12 Claims, 6 Drawing Figures

```
            1                                              15
  <Glu-Asp-Asn-Ser-Arg-Tyr-Thr-His-Phe-Leu-Thr-Gln-His-Tyr-Asp-
                                                           30
    Ala-Lys-Pro-Gln-Gly-Arg-Asp-Asp-Arg-Tyr-Cys-Glu-Ser-Ile-Met-
                                                           45
    Arg-Arg-Arg-Gly-Leu-Thr-Ser-Pro-Cys-Lys-Asp-Ile-Asn-Thr-Phe-
                                                           60
    Ile-His-Gly-Asn-Lys-Arg-Ser-Ile-Lys-Ala-Ile-Cys-Glu-Asn-Lys-
                                                           75
    Asn-Gly-Asn-Pro-His-Arg-Glu-Asn-Leu-Arg-Ile-Ser-Lys-Ser-Ser-
                                                           90
    Phe-Gln-Val-Thr-Thr-Cys-Lys-Leu-His-Gly-Gly-Ser-Pro-Trp-Pro-
                                                          105
    Pro-Cys-Gln-Tyr-Arg-Ala-Thr-Ala-Gly-Phe-Arg-Asn-Val-Val-Val-
                                                          120
    Ala-Cys-Glu-Asn-Gly-Leu-Pro-Val-His-Leu-Asp-Gln-Ser-Ile-Phe-
              123
    Arg-Arg-Pro-OH.
```

FIG. 1

1
<Glu-Asp-Asn-Ser-Arg-Tyr-Thr-His-Phe-Leu-Thr-Gln-His-Tyr-Asp-
                                                              15
Ala-Lys-Pro-Gln-Gly-Arg-Asp-Asp-Arg-Tyr-Cys-Glu-Ser-Ile-Met-
                                                              30
Arg-Arg-Arg-Gly-Leu-Thr-Ser-Pro-Cys-Lys-Asp-Ile-Asn-Thr-Phe-
                                                              45
Ile-His-Gly-Asn-Lys-Arg-Ser-Ile-Lys-Ala-Ile-Cys-Glu-Asn-Lys-
                                                              60
Asn-Gly-Asn-Pro-His-Arg-Glu-Asn-Leu-Arg-Ile-Ser-Lys-Ser-Ser-
                                                              75
Phe-Gln-Val-Thr-Thr-Cys-Lys-Leu-His-Gly-Gly-Ser-Pro-Trp-Pro-
                                                              90
Pro-Cys-Gln-Tyr-Arg-Ala-Thr-Ala-Gly-Phe-Arg-Asn-Val-Val-Val-
                                                              105
Ala-Cys-Glu-Asn-Gly-Leu-Pro-Val-His-Leu-Asp-Gln-Ser-Ile-Phe-
123                                                           120
Arg-Arg-Pro-OH.

```
 597  CCTTCCATTT CCCCTCTGCA CCCAGAACAG TGGTGGCAAC ATTCATTGCC AAGGGCCCAA AGAAAGAGCT ACCTGGACCT TTTGTTTTCT GTTTGACAAC
 697  ATGTTTATA ATAAAAATG TCTTGATATC AGTAAGAATC AGAGTCTTCT CACTGATATTG GGGCATATTG ATCTTTCCCC CATTTTCTCT ACTTGGCTGC
 797  TCCCTGAGAG GACTGCATAG GATAGAAATG CCTTTTTCTT TTTTTTTCGT TTTTTTTTT TTTTTTTTT GAGATGGAGT CTCACTCTGT CGCCCAGGCT
 897  TAAGTGCAAT GGCACAATCT CGGCTCACTG CAACCTCTCT CTCCGGGTT CAAGTGATTC TCCTGCCTCA GCCTCCCAAA TAGCTGAGAT TACAGGCATG
 997  CACCACCACA CCTGGCTAAT TTTTGTGTT TTAGTAGAGA CAGGGTTTCA CCGTTTGGTC CCAGGCTGGTC TTGAACTCCT GACCTCGGGA GATCCGCCCA
1097  CCTTGGCCTC TCTTTGTGCT TCTTTTTTC CCACTTTTC CTTATCAGTC AGTTTTACA AGTCATTAGG GAGGTAGACT
1197  TTACCTCTCT GTGAAGGAAA GTATGGTATG TTGATCTACA GAGAGAGATG AGGGCTCGTA GCTACTAAGC AGAATTTCCA AGATAGGCAA
1297  ATGTTTTT CTGTCAAATA ATAAGCTAAT ATTACTTCTA CAAATATGAG ACCTGGAGA GAAGTTTCCA AGGACCAAGT ACCAACATAC CAACAGATTA
1397  TTATAGTTTC TCTCACTCTT ACACACACAC ACACATATAT ACACATATGT GATATTCTCT TGTCATGGTT ATTTTATATA AAATCAAAA TTATTCCTC
1497  ATCGAGAGAT AATTTTGATG TTTGAATGA ACTAATGTCT GGCAAGTGTG ATGTTTTGGG GAAGTTATAG AAGATTCCG CCAGGCGCTT ATCTCACGCT TGTAATCCAG
1597  TGTAATCTTT TACTTTATCA ACTAATGTCT GGCAAGTGTG ATGTTTTGGG GAAGTTATAG AAGATTCCG CCAGGCGCTT ATCTCACGCT TGTAATCCAG
1697  CACTTTGGGA AGCTGAGGCG GACAGATCAC GAGGTCAAGA GATCAAGACC ATCCTGGACA ACATGGTGAA ACCTTGTCTC TACTAAAAT GTGAAAATTA
1797  GCTGGGCGTG GTGGCACACA CCTATAGTCC CAGCTACTCG CAGGAGGCTG AGGCAGGAGA CGCTTGAACC TAGGAGGCGG AGTTGCACT GAGCCGAGAT
1897  CACGCCACTG CACTCCAGCC TGGGCGACAG AGCGAGACTC CATCTCAAAA AAAAAAAAA CTCTTTGTAA AATACACTGT ATTAGTTATA AGTCGCCAGT TTAGCTTCCT
1997  CCTCAATTCT CAAGATTTGT TTTTAAGTTA ACATAACTTA AGGTACTTGG ATATTTTATT TAGAAAGTGG TTGCCAATAA ATTAGTTATA AGTCGCCAGT TCACTGCCT TGTGAACACA
2097  GTTAACTAAT TCTGTTGAC AGGTACTTGG ATATTTTATT TAGAAAGTGG TTGCCAATAA ATTAGTTATA AGTCGCCAGT TCACTGCCT TGTGAACACA
2197  TAATTATTGT GGTCTCAGTA TTCCCTATGG TGGCTTCTC TGCTCCTGGT ATGCCCCTGA AATGGGCCAA AAGCCGTGC TCCCAATGC TCAGTTATA
2297  GAACATTGTC CAGGAGAGC CCAGCCTCAC CTAGGAGAGC CCAGCCTCAC TGAAAGTATT CAAATTTAGG AATGGGTTTG AGAAGTAGGT AGCTGGTATG TGCTTAGCAC
2397  AAGAATCTCT CTTCCTTGGG TTAGTCTCGT TCAAAACTGA AACACACTGTC ATTCCTAAG AAAATAGGAA AAGTATTCC AACCTCTGT CACTAGAAA
```

CDNA AND GENE FOR HUMAN ANGIOGENIN (ANGIOGENESIS FACTOR) AND METHODS OF EXPRESSION

This application is a continuation-in-part of our copending application U.S. Ser. No. 770,657 filed Aug. 28, 1985, which is hereby incorporated by reference.

FIELD OF THE INVENTION

This invention relates to protein production through recombinant DNA techniques. More particularly, it relates to DNA sequences encoding proteins having angiogenic activity and to methods of expressing those sequences.

BACKGROUND ART

Angiogenesis, the process of developing a hemovascular network, is essential for the growth of solid tumors and is a component of normal wound healing and growth processes. It has also been implicated in the pathophysiology of atherogenesis, arthritis, and diabetic retinopathy. It is characterized by the directed growth of new capillaries toward a specific stimulus. This growth, mediated by the migration of endothelial cells, may proceed independently of endothelial cell mitosis.

The molecular messengers responsible for the process of angiogenesis have long been sought. Greenblatt and Shubik (*J. Natl. Cancer Inst.* 41: 111-124, 1968) concluded that tumor-induced neovascularization is mediated by a diffusible substance. Subsequently, a variety of soluble mediators have been implicated in the induction of neovascularization. These include prostaglandins (Auerbach, in *Lymphokines*, Pick and Landy, eds., 69-88, Academic Press, New York, 1981), human urokinase (Berman et al., *Invest Opthalm. Vis. Sci.* 22: 191-199, 1982), copper (Raju et al., *J. Natl. Cancer Inst.* 69: 1183-1188, 1982), and various "angiogenesis factors".

Angiogenesis factors have been derived from tumor cells, wound fluid (Banda et al., *Proc. Natl. Acad. Sci USA* 79: 7773-7777, 1982; Banda et al., U.S. Pat. No. 4,503,038), and retinal cells (D'Amore, *Proc. Natl. Acad. Sci. USA* 78: 3068-3072, 1981). Tumor-derived angiogenesis factors have in general been poorly characterized. Folkman et al. (*J. Exp. Med.* 133: 275-288, 1971) isolated tumor angiogenesis factor from the Walker 256 rat ascites tumor. The factor was mitogenic for capillary endothelial cells and was inactivated by RNase. Tuan et al. (*Biochemistry* 12: 3159-3165, 1973) found mitogenic and angiogenic activity in the nonhistone proteins of the Walker 256 tumor. The active fraction was a mixture of proteins and carbohydrate. A variety of animal and human tumors have been shown to produce angiogenesis factor(s) (Phillips and Kumar, *Int. J. Cancer* 23: 82-88, 1979) but the chemical nature of the factor(s) was not determined. A low molecular weight non-protein component from Walker 256 tumors has also been shown to be angiogenic and mitogenic (Weiss et al., *Br. J. Cancer* 40: 493-496, 1979). An angiogenesis factor with a molecular weight of 400-800 daltons was purified to homogeneity by Fenselau et al. (*J. Biol. Chem.* 256: 9605-9611, 1981), but it was not further characterized. Human lung tumor cells have been shown to secrete an angiogenesis factor comprising a high molecular weight carrier and a low molecular weight, possibly non-protein, active component (Kumar et al., *Int. J. Cancer* 32: 461-464, 1983). Vallee et al. (*Experientia.* 41: 1-15, 1985) found angiogenic activity associated with three fractions from Walker 256 tumors. Tolbert et al. (U.S. Pat. No. 4,229,531) disclose the production of angiogenesis factor from the human adenocarcinoma cell line HT-29, but the material was only partially purified and was not chemically characterized. Isolation of genes responsible for the production of angiogenesis factors has not heretofore been reported at least in part due to the lack of purity and characterization of the factors.

Isolation of angiogenesis factors has employed high performance liquid chromatography (Banda et al., ibid); solvent extraction (Folkman et al., ibid); chromatography on silica gel (Fenselau et al., ibid), DEAE cellulose (Weiss et al., ibid), or Sephadex (Tuan et al., ibid); and affinity chromatography (Weiss et al., ibid).

Recently, Vallee et al. (U.S. patent application Ser. No. 724,088, filed Apr. 17, 1985, and U.S. Ser. No. 778,387, filed concurrently with this application, both of which are hereby incorporated by reference) have purufied an angiogenic protein from a human adenocarcinoma cell line. The purified protein, known as angiogenin, was chemically characterized and its amino acid sequence determined.

Because angiogenesis factors play an important role in wound healing (Rettura et al., FASEB Abstract #4309, 61st Annual Meeting, Chicago, 1977) and may find applicability in the development of screening tests for malignancies (Klagsburn et al., *Cancer Res.* 36: 110-114, 1976; and Brem et al., *Science* 195: 880-881, 1977), it would clearly be advantageous to produce angiogenic proteins in sufficient quantities to permit their application in therapy and diagnosis. The techniques of genetic engineering are ideally suited to increase production levels of these proteins. The cloning of genes encoding angiogenic proteins is a necessary first step in such a large-scale production.

Furthermore, it may in some instances be desirable to obtain these proteins from non-tumor cells, such as in the case of human therapeutics, where contamination with certain tumor products would be unacceptable. This invention therefore provides for the production of angiogenic proteins in non-tumor cells using recombinant DNA techniques.

DISCLOSURE OF THE INVENTION

Briefly stated, the present invention discloses a DNA sequence encoding a protein having angiogenic activity. A DNA sequence encoding angiogenin, or a protein having substantially the same biological activity as angiogenin, is also disclosed. The DNA sequences may be obtained from cDNA or genomic DNA, or may be prepared by DNA synthesis techniques.

The invention further discloses vectors comprising a DNA sequence encoding a protein having angiogenic activity. Vectors comprising a DNA sequence encoding a protein having substantially the same biological activity as angiogenin are also disclosed. The vectors further comprise a promoter sequence upstream of and operably linked to the DNA sequence. In general, the vectors will also contain a selectable marker, and, depending on the host cell used, may contain such elements as regulatory sequences, polyadenylation signals, enhancers, and RNA splice sites.

An additional aspect of the present invention discloses cells transfected or transformed to produce a protein having angiogenic activity. Cells transfected or transformed to produce a protein having substantially the same biological activity as angiogenin are also disclosed. The cells are transfected or transformed to contain an expression vector comprising a DNA sequence encoding a protein having angiogenic activity.

A further aspect of the present invention discloses a method for producing a protein having angiogenic activity. The method comprises (a) introducing into a host cell a vector comprising a DNA sequence encoding a protein having angiogenic activity; (b) growing the host cell in an appropriate medium; and (c) isolating the protein product encoded by the DNA sequence and produced by the host cell. A method for producing a protein having substantially the same biological activity as angiogenin is also disclosed. The proteins produced by these methods are also disclosed.

Other aspects of the invention will become evident upon reference to the detailed description and drawings.

BRIEF DESCRIPTION OF THE DRAWINGS

FIG. 1 illustrates the amino acid sequence of angiogenin purified from human adenocarcinoma HT-29 cells.

FIG. 3 illustrates a portion of the sequence of the genomic DNA insert in λHAG1. The cDNA insert of pHAG1 corresponds to nucleotides 106 to 731 of the genomic DNA, with a substitution at nucleotide 252.

BEST MODE FOR CARRYING OUT THE INVENTION

Figure 2:
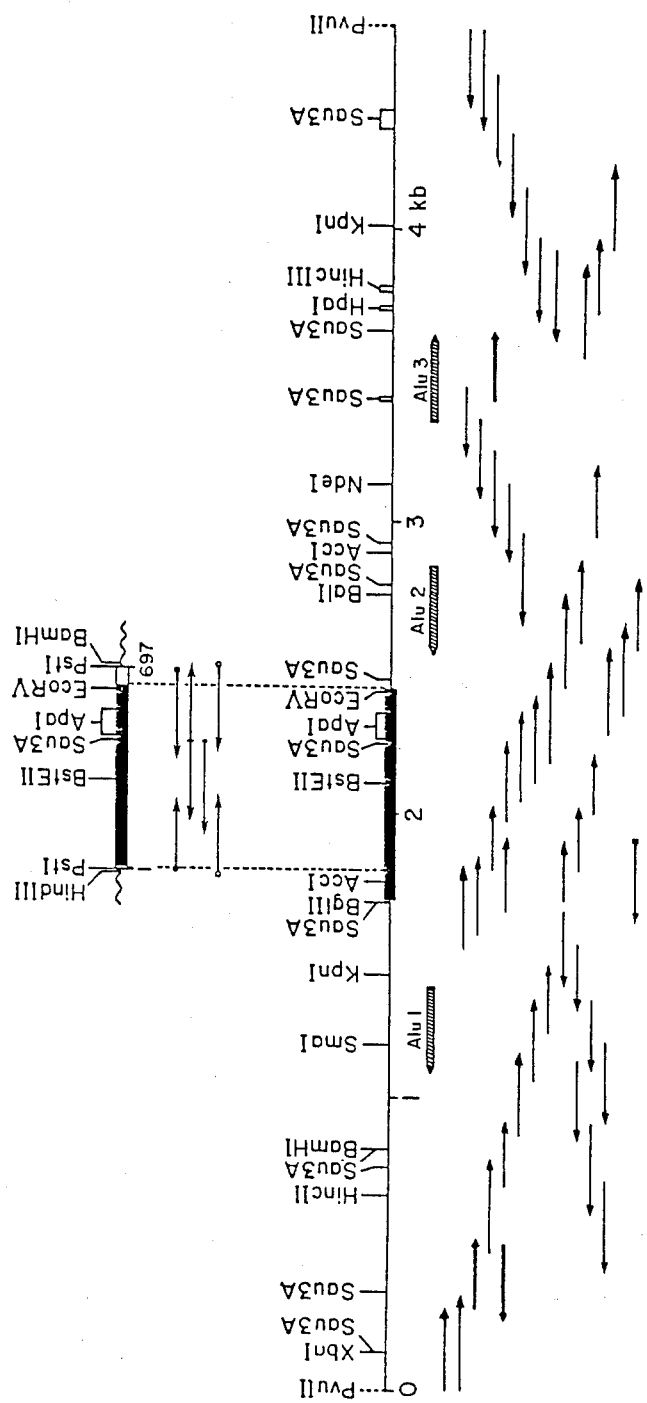
FIG. 2 illustrates the strategy used for sequencing the angiogenin cDNA and genomic clones. The top portion refers to the cDNA and the bottom portion to the genomic DNA. Solid bars indicate the coding regions, arrows indicate the fragments sequenced. The locations and directions of the three Alu sequences are indicated by large hatched arrows.

Prior to setting forth the invention, it may be helpful to define certain terms to be used hereinafter.

Biological activity is a function or set of functions performed by a molecule in a biological context (i.e., in an organism or an in vitro facsimile). For angiogenin, biological activity is characterized by its angiogenic activity.

Angiogenic activity is the chemical stimulation of hemovascular development in tissue. It is generally associated with diffusible substances produced by a variety of cell types. Angiogenic activity may be characterized by a positive response in the chick embryo chorioallantoic membrane assay (Knighton et al., *Br. J. Cancer* 35: 347–356, 1977) and/or the rabbit cornea implant assay (Langer and Folkman, *Nature* 263: 797–800, 1976).

DNA construct is a DNA molecule, or a clone of such a molecule, which has been modified by human intervention to contain segments of DNA which are combined and juxtaposed in a manner which would not otherwise exist in nature.

Angiogenic proteins are produced by a variety of cell types, including tumor cells and retinal cells. Until recently, these proteins have not been obtained in sufficient purity to permit their chemical and physical characterization. Through the application of a novel multi-step purification procedure, an exemplary angiogenic protein, hereinafter angiogenin, has been purified from culture media of a human tumor cell line. Determination of the protein sequence has allowed the isolation of corresponding DNA sequences and the expression of these sequences through recombinant DNA techniques.

The isolation of angiogenic proteins is based on the fractionation of conditioned cell media by ion exchange chromatography, followed by high performance liquid chromatography.

Although tumor cells are the preferred source of an angiogenic protein according to the present invention, other types of cells, notably retinal cells, are known to produce angiogenesis factors. A particularly preferred cell line is the human adenocarcinoma cell line HT-29 (Fogh and Trempe, in *Human Tumor Cells in Vitro*, Fogh, ed., 115–160, Plenum, New York, 1975). HT-29 isolates have been deposited with American Type Culture Collection under accession numbers HTB38 and CRL8905. The cells may be cultured according to known methods, e.g. as monolayer cultures in Dulbecco's modified Eagle's medium or other suitable media. A preferred medium is Dulbecco's modified Eagle's medium supplemented with 2 mM L-glutamine and 5% heat inactivated fetal bovine serum (DME/5). The medium is changed periodically and cells are subcultured according to known procedures.

To facilitate isolation of angiogenic protein(s) from the cell medium, it is preferred that the cells be transferred to a serum free maintenance medium once they have reached confluent growth. A preferred maintenance medium is DME/5 without serum but containing L-glutamine at a concentration of 5 mM.

Medium in which cells have been cultured or maintained, known as conditioned medium, is then removed from the cells and preferably filtered to remove cell debris, then treated to remove high molecular weight proteins. A preferred method of treatment of acidification, e.g. by the addition of glacial acetic acid to a concentration of 5% (v/v), followed by centrifugation. It may also be desirable to concentrate the filtered, acidified medium prior to further purification steps.

The filtered treated medium is then chromatographed on a cation exchange matrix, such as carboxymethyl cellulose (CM cellulose). It is preferred that the treated, conditioned medium be lyophilized, reconstituted in 0.1M sodium phosphate buffer pH 6.6, and applied to the matrix. Under such conditions, the angiogenesis factor(s) will bind to the matrix and may be eluted with the same buffer containing 1M NaCl.

The eluate from the cation exchange matrix is further fractionated by reversed-phase high performance liquid chromatography. The eluate is lyophilized, reconstituted in a suitable solvent, such as 0.1% trifluoroacetic acid (TFA) in water, and eluted by applying a gradient of a second solvent to the column. A linear gradient of isopropanol/acetonitrile/water (5:5:4 v/v/v) containing 0.08% TFA is preferred. Material eluted from the HPLC column may then be dialyzed to remove the solvent, lyophilized, and reconstituted.

The reconstituted HPLC column eluate is then assayed for angiogenic activity to identify the active fraction(s). Several assays for angiogenic activity are well known in the art, including the chick embryo chorioallantoic membrane assay (Knighton et al., *Br. J. Cancer* 35: 347–356, 1977) and the cornea implant assay (Langer and Folkman, *Nature* 263: 797–800, 1976).

When HT-29 cells are employed as the starting material, two active fractions are obtained from the HPLC column. One fraction contains a major protein component of $M_r \sim 16,000$ and lesser amounts of a $M_r \sim 14,000$ species. The second fraction contains a single protein species of $M_r \sim 14,000$, which has been designated angiogenin. On further analysis, angiogenin was found to have an isoelectric point greater than 9.5 and a molecular weight of approximately 14,193 daltons by amino acid sequence analysis. Surprisingly, in contrast to most previously described angiogenesis factors, angiogenin is not mitogenic in conventional assays. The amino acid sequence of angiogenin was found to be 35% homologous to the pancreatic ribonucleases.

When an angiogenic protein has been obtained in substantially pure form, its amino acid sequence is determined by known methods, for example, Edman degradation (Edman and Begg, *Eur. J. Biochem.* 1: 80–91, 1967). It is not necessary to determine the entire amino acid sequence. Preferably, a sequence of at least 5–10 amino acids will be determined.

From the amino acid sequence, a DNA probe is designed. Generally, it will be necessary to design a family of probes corresponding to all of the possible DNA sequences encoding the amino acid sequence. It is preferred that such a probe be at least 14 nucleotides in length in order to minimize false positive signals when screening DNA clones. Suitable probes may be synthesized by known methods (for review, see Itakura, in *Trends in Biochemical Science,* Elsevier Biochemical Press, 1982) or purchased from commercial suppliers.

cDNA (complementary DNA) and/or genomic DNA libraries are then prepared and screened with the probe(s) using conventional hybridization techniques. Techniques for preparing such libraries are well known in the art (see, for example, Lawn et al., *Cell* 15: 1157–1174, 1978; and Michelson et al., *Proc. Natl. Acad. Sci. USA* 80: 472–476, 1983). Clones which hybridize to the probe(s) are then selected and sequenced.

Alternatively, if a sufficient quantity of pure angiogenic protein is obtained, it may be used to prepare an antibody, and the antibody in turn used to screen an expression cDNA library (Young and Davis, *Pro. Natl. Acad. Sci. USA* 80: 1194–1198, 1983).

If a full length cDNA clone is obtained, it may be inserted directly into an expression vector for use in producing the angiogenic protein. Lacking a full length cDNA clone, the remaining coding sequence may be obtained by several methods, and a full length coding sequence may then be constructed. A cDNA clone may be used as a probe to screen additional cDNA libraries or to screen genomic DNA libraries. If the amino acid sequence of the protein is known, the missing material may be synthesized and joined to the cDNA and/or genomic DNA fragments to construct a complete coding sequence. Under some circumstances, it is preferred that the coding sequence further encode a leader peptide in order to facilitate proper processing and secretion of the angiogenic protein produced according to the present invention. The leader peptide may be that of the angiogenic peptide itself, or a heterologous leader peptide which functions in the particular host cell.

When a full length DNA sequence encoding an angiogenic protein has been obtained, it is then inserted into a suitable expression vector. Expression vectors for use in carrying out the present invention will further comprise a promoter operably linked to the DNA sequence encoding the angiogenic protein. In some instances it is preferred that expression vectors further comprise an origin of replication, as well as sequences which regulate and/or enhance expression levels, depending on the host cell selected. Suitable expression vectors may be derived from plasmids or viruses, or may contain elements of both.

Preferred prokaryotic hosts for use in carrying out the present invention are strains of the bacteria *Escherichia coli,* although Becillus and other genera are also useful. Techniques for transforming these hosts and expressing foreign genes cloned in them are well known in the art (see, for example, Maniatis et al., *Molecular Cloning: A Laboratory Manual,* Cold Spring Harbor Laboratory, 1982). Vectors used for expressing foreign genes in bacterial hosts will generally contain a selectable marker, such as a gene for antibiotic resistance, and a promoter which functions in the host cell. Appropriate promoters include the trp (Nichols and Yanofsky, *Meth. in Enzymology* 101: 155, 1983) lac (Casadaban et al., *J. Bact.* 143: 971–980, 1980) and phage λ promoter systems. Plasmids useful for transforming bacteria include pBR322 (Bolivar, et al., *Gene* 2: 95–113, 1977), the pUC plasmids (Messing, *Meth. in Enzymology* 101: 20–77, 1983; and Vieira and Messing, *Gene* 19: 259–268, 1982), pCQV2 (Queen, *J. Mol. Appl. Genet.* 2: 1–10, 1983), and derivatives thereof.

Eukaryotic microorganisms, such as the yeast *Saccharomyces cerevisiae,* may also be used as host cells. Techniques for transforming yeast are described by Beggs (*Nature* 275: 104–108, 1978). Expression vectors for use in yeast include YRp7 (Struhl et al., *Proc. Natl. Acad. Sci. USA* 76: 1035–1039, 1979). YEp13 (Broach et al., *Gene* 8: 121–133, 1979), pJDB248 and pJDB219 (Beggs, ibid), and derivatives thereof. Such vectors will generally comprise a selectable marker, such as the nutritional marker TRP, which allows selection in a host strain carrying a trp1 mutation. Preferred promoters for use in yeast expression vectors include promoters from yeast glycolytic genes (Hitzeman et al., *J. Biol. Chem.* 255: 12073–12080, 1980; Alber and Kawasaki, *J. Mol. Appl. Genet.* 1: 419–434, 1982) or alcohol dehydrogenase genes (Young et al., in *Genetic Engineering of Microorganisms for Chemicals,* Hollaender et al., eds., p. 335, Plenum, New York, 1982; and Ammerer, *Meth. in Enzymology* 101: 192–201, 1983). To facilitate purification of an angiogenic protein produced in a yeast transformant and obtain proper disulphide bond formation, a signal sequence, preferably from a yeast gene encoding a secreted protein, may be joined to the coding sequence for the angiogenic protein. A particularly preferred signal sequence is the pre-pro region of the MFα1 gene (Kurjan and Herskowitz, *Cell* 30: 933–943, 1982).

Higher eukaryotic cells may also serve as host cells in carrying out the present invention. Cultured mammalian cells are preferred. Expression vectors for use in mammalian cells will comprise a promoter capable of directing the transcription of a foreign gene introduced into a mammalian cell. A particularly preferred promoter is the mouse metallothionein-1 (MT-1) promoter (Palmiter et al., *Science* 222: 809–814, 1983). Also contained in the expression vectors is a polyadenylation signal, located downstream of the insertion site. The polyadenylation signal may be that of the cloned angiogenic protein gene, or may be derived from a heterologous gene.

Cloned gene sequences may then be introduced into cultured mammalian cells by, for example, calcium phosphate-mediated transfection (Wigler et al., *Cell* 14: 725, 1978; Coraro and Pearson, *Somatic Cell Genetics* 7: 603, 1981; Graham and Van der Eb, *Virology* 52: 456, 1973). A precipitate is formed of the DNA and calcium phosphate, and this precipitate is applied to the cells. Some of the cells take up the DNA and maintain it inside the cell for several days. A small fraction of these cells (typically $10^{-4}$) integrate the DNA into the genome. In order to identify these integrants, a gene that confers a selectable phenotype (a selectable marker) is generally introduced into the cells along with the gene of interest. Preferred selectable markers include genes that confer resistance to drugs, such as neomycin, hygromycin, and methotrexate. Selectable markers may be introduced into the cell on a separate plasmid at the same time as the gene of interest, or they may be introduced on the same plasmid.

The copy marker of the integrated gene sequence may be increased through amplification by using certain selectable markers (e.g., dihydrofolate reductase, which confers resistance to methotrexate). The selectable marker is introduced into the cells along with the gene of interest, and drug selection is applied. The drug concentration is then increased in a step-wise manner, with selection of resistant cells at each step. By selecting for increased copy number of cloned sequences, expression levels may be substantially increased.

Angiogenic proteins produced according to the present invention may be purified form the host cells or cell media by cation exchange chromatography and high performance liquid chromatography as described above.

It will be appreciated that other angiogenic proteins may be isolated by the above process. Different cell lines may be expected to produce angiogenic proteins having different physical properties. Additionally, variations may exist due to genetic polymorphisms or cell-mediated modifications of the proteins or their precursors. Furthermore, the amino acid sequence of an angiogenic protein may be modified by genetic techniques to produce proteins with altered biological activities. For example, based on the homology between antiogenin and ribonuclease, the cys residues at positions 26, 39, 57, 81, 92 and 107, and histidines at positions 13 and 114, and the lysine at position 40 are preferred sites for replacement by other amino acids by site specific mutagenesis (Zoller et al., *Manual for Advanced Techniques in Molecular Cloning Course*, Cold Spring Harbor Laboratory, 1983). The resultant DNA sequence will encode a protein having substantially the same amino acid sequence as angiogenin, but exhibiting a higher or lower level of angiogenic activity. An increase in the biological activity could permit the use of lower dosage levels. A molecule having reduced angiogenic activity or no angiogenic activity, but retaining certain structural features, could still bind receptors on endothelial or other cells and, by blocking the site of action, form an antagonist to the action of the natural protein, resulting in an approach to the treatment of angiogenesis-related disease states. Such proteins are within the scope of the present invention.

Angiogenic proteins produced according to the present invention may be used to produce therapeutic or diagnostic compositions by combining them with suitable carriers. The therapeutic compositions may be used to promote the development of a hemovascular network in a mammal, for example, to induce collateral circulation following a heart attack, or to promote wound healing, for example in joints or other locations. Preferably, the therapeutic compositions according to the present invention will be administered intravenously or by direct topical application to the wound site. For example, if injury occurs to the meniscus of the knee or shoulder as frequently occurs in sports-related injuries or osteoarthritis, injection of angiogenic proteins at the site of the injury may promote healing of torn or traumatized fibrocartilage material. Effective doses will vary according to the severity of the condition and the target tissue. Furthermore, angiogenic proteins have diagnostic applications in screening for the presence of malignancies, either by using the protein to assay for the presence of antibodies or to produce antibodies for use as immunodiagnostic reagents. A diagnostic composition containing the protein may be incubated with a biological sample under conditions suitable for the formation of an antigen-antibody complex. The formation of the complex (i.e., the presence of antibodies in the sample) is then detected. Techniques for such assays are well known in the art, e.g. the enzyme linked immunosorbent assay (Voller et al., *The Enzyme Linked Immunosorbent Assay*, Dynatech Laboratories, Inc., 1979) or the Western blot assay (see, for example, Towbin et al., *Proc. Natl Acad. Sci. USA* 76: 4350, 1979). Similarly, a diagnostic composition comprising an antibody against an angiogenic protein may be used to assay for the presence of the protein in a biological sample. The angiogenic proteins may also be used to develop angiogenesis inhibitors which may be useful in the treatment of disorders associated with angiogenesis. Recombinant DNA provides a superior method for the production of these proteins in the quantities needed for these applications.

EXPERIMENTAL

Materials and Methods

Restriction endonucleases, T4 DNA ligase, T4 kinase, alkaline phosphatase, endonuclease Bal 31 and Klenow fragment of DNA polymerase I (*E. coli*) were purchased from Bethesda Research Laboratories or New England Biolabs. Reverse transcriptase (avain myeloma virus) was obtained from Seikagaku U.S.A., Inc. Dideoxynucleotide triphosphates, deoxynucleotide triphosphates, pBR322 and pUC13 were purchased from P-L Biochemicals. Universal primers (hepta decamer) for dideoxy sequencing were purchased from New England Biolabs, and the $[\alpha\text{-}^{32}P]dATP$, $[\gamma^{32}P]ATP$, and $[^{35}S]dATP\alpha S$ were obtained from Amersham.

EXAMPLE 1

Isolation of cDNA and Genomic Sequences Encoding Angiogenin

A human cDNA library was prepared from human liver poly(A)-mRNA employing plasmid pUC13 as a cloning vector (Maniatis et al., ibid). This plasmid was previously tailed with G's at its PstI site (Michelson & Orkin, 1982). A mixture of 26 synthetic oligonucleotides [CCCTGAGGCTTAGC(A/G)TC(A/G)TA(A/G)TG(C/T)TG] was purchased from P-L Biochemicals and employed as a hybridization probe. The nucleotide mixture is complementary to nucleotide sequences that code for Gln-His-Tyr-Asp-Ala-Lys-Pro-Gln-Gly. This sequence is present in the amino-terminal region of human angiogenin isolated from the colon adenocarcinoma cell line HT-29 (see FIG. 1). The nucleotide mixture was radiolabeled with T4 kinase and $[^{32}P]ATP$ to a specific activity of approximately $3 \times 10^8$ cpm/$\mu$g and employed for the screening of 350,000 transformants from the liver library by the method of Wallace et al. (*Nucleic Acids Res.* 9: 879–894, 1981). Seven recombinant plasmids that hybridized strongly with the probe were isolated and purified by cesium chloride gradient centrifugation. The DNA inserts in each of the positive clones were digested with various restriction enzymes and analyzed by polyacrylamide gel electrophoresis. Their sequence was determined by the chemical degradation method of Maxam & Gilbert (*Meth. in Enzymology* 65: 499–560, 1980). Each sequence was determined two or more times, and greater than 85% of the sequence was determined on both strands.

The plasmid containing the largest cDNA insert (pHAG1) was then sequenced by the method of Maxam & Gilbert (ibid) according to the strategy shown in the top of FIG. 2. This cDNA insert contained 697 nucleotides and included 12 G's at the 5' end, a short noncoding sequence, a leader sequence coding for a signal peptide of 24 (or 22) amino acids, 369 nucleotides coding for the mature protein of 123 amino acids, a stop codon, 175 nucleotides of 3' noncoding sequence, a poly(A) tail of 36 nucleotides, and 23 C's on the 3' end. The cDNA insert corresponds to nucleotides 106 to 731 of the genomic DNA sequence shown in FIG. 3, with a substitution at nucleotide 252 (encoding a Gly at residue 23). Plasmid pHAG1 has been deposited with American Type Culture Collection under accession number 40192.

A human genomic library (Maniatis et al., *Cell* 15: 687–702, 1978) consisting of about $3 \times 10^6$ $\lambda$ Charon 4A bacteriophage was screened with the cDNA insert of clone pHAG1 which had been radiolabeled by nick translation (Rigby et al., *J. Mol. Biol.* 113: 237–251, 1977). One strongly hybridizing phage clone, designated $\lambda$HAG1, identified by the method of Benton & Davis (*Science* 196: 181–182, 1977) was plaque purified, and the phage DNA was isolated by the plate lysis method (Maniatis et al., 1982, ibid). The genomic insert was analyzed by digestion with various restriction enzymes. A DNA fragment generated by digestion of the insert with PvuII was about 5 kilo bases in size and strongly hybridized to the cDNA probe. This fragment was subcloned into plasmid pBR322 and subjected to DNA sequencing by the dideoxy method (Messing et al., *Nucleic Acids Res.* 9: 309–321, 1981; Norrander et al., *Gene* 26: 101–106, 1983) employing [$^{35}$S]dATP$\alpha$S as described in the Amersham cloning and sequencing manual. A ~3 kb DNA fragment generated by digestion of the phage genomic insert with KpnI which strongly hybridized to the probe was subcloned into the M13mp18 phage vector and subjected to DNA sequencing employing the synthetic oligonucleotide probe as a primer. Systematic deletions of the genomic DNA with endonuclease Bal 31 were carried out essentially as described by Poncz et al. (*Proc. Natl. Acad. Sci. USA* 79: 4298–4302, 1982), Guo & Wu (*Meth. in Enzymology* 100: 60–96, 1983). About 95% of the genomic DNA sequence was determined two or more times, and greater than 50% of the genomic sequence was determined on both strands. A portion of this sequence corresponded to the coding sequence for angiogenin. The vector $\lambda$HAG1 has been deposited with American Type Culture Collection under accession number 40193.

The gene for angiogenin was also found in a DNA fragment of about 5 kilo bases that was generated by digestion of $\lambda$HAG1 with PvuII. This DNA fragment was subcloned into pBR322 and subjected to DNA sequencing by the dideoxy chain termination method employing the strategy shown in the bottom of FIG. 2. The complete sequence of the gene for human angiogenin (FIG. 3) indicated that the gene contains about 800 nucleotides and is free of intervening sequences in the coding and 3' noncoding regions of the gene. The possibility of an intron(s) in the 5' flanking region cannot be excluded, however, since the largest cDNA did not extend into this region.

The gene for angiogenin contains three Alu repetitive sequences (Schmid & Jelinek, *Science* 216: 1065–1070, 1982) in its flanking regions (FIGS. 2 and 3). The first Alu repeat was located in the immediate 5' flanking region of the gene, while the second was present in the immediate 3' flanking region. These two Alu repeats were in the same inverted orientation. The third Alu repeat was located about 500 nucleotides downstream from the second Alu sequence in the 3' flanking region of the gene and was in the typical orientation with the poly(A) on the 3' end of the 300 nucleotide sequence. Furthermore, each Alu repeat was flanked by a pair of short direct repeat sequences. The nucleotide sequences for the three Alu repeats were about 87% homologous to the consensus Alu sequence of Schmid & Jelinek (ibid).

A tentative TATA box (Goldberg, M. L., Doctoral Dissertation, Stanford University, 1979) and a transcription initiation site were identified at nucleotides $-32$ and $+1$ respectively, but no potential CAAT box was found in the immediate vicinity. A sequence of TCAAT was identified, however, at nucleotide $-255$ which is about 190 bp upstream from the proposed TATA box. Two sequences of AATAAA which are involved in the polyadenylation or processing of the messenger RNA at the 3' end (Proudfoot & Brownlee, *Nature* 263: 211–214, 1976), were identified at nucleotides 703 and 707. Polyadenylation of the mRNA occurs at nucleotide 731 which is 20 nucleotides downstream from the end of the second AATAAA sequence. The consensus sequence of CACTG, which also may be involved in polyadenylation or cleavage of the mRNA at the 3' end (Berget, *Nature* 309: 179–182, 1984), was present starting at nucleotide 747. A stretch of 32 nucleotides with alternating purine and pyrimidine was found starting with nucleotide 1416. This sequence provides a potential region for a left-handed helix structure or Z-DNA in the gene Rich et al., *Ann. Rev. Biochem.* 53: 791–846, 1984). A computer search of the flanking regions of the gene for angiogenin as well as in the complementary strand showed no open reading frames.

The amino acid sequence of human angiogenin is about 35% homologous with human ribonuclease. The location of the disulfide bonds, determined by direct protein sequence analysis, further emphasizes the homology to ribonuclease.

EXAMPLE 2

Production of Angiogenin in Transfected Mammalian Cells

For expressing angiogenin in transfected mammalian cells, expression vector pHAGF-MT-DHFR, comprising the angiogenin genomic coding sequence (HAGF), the mouse metallothionein-1 (MT-1) promoter, and a DHFR selectable marker joined to the SV40 promoter, was constructed.

Figure 4:
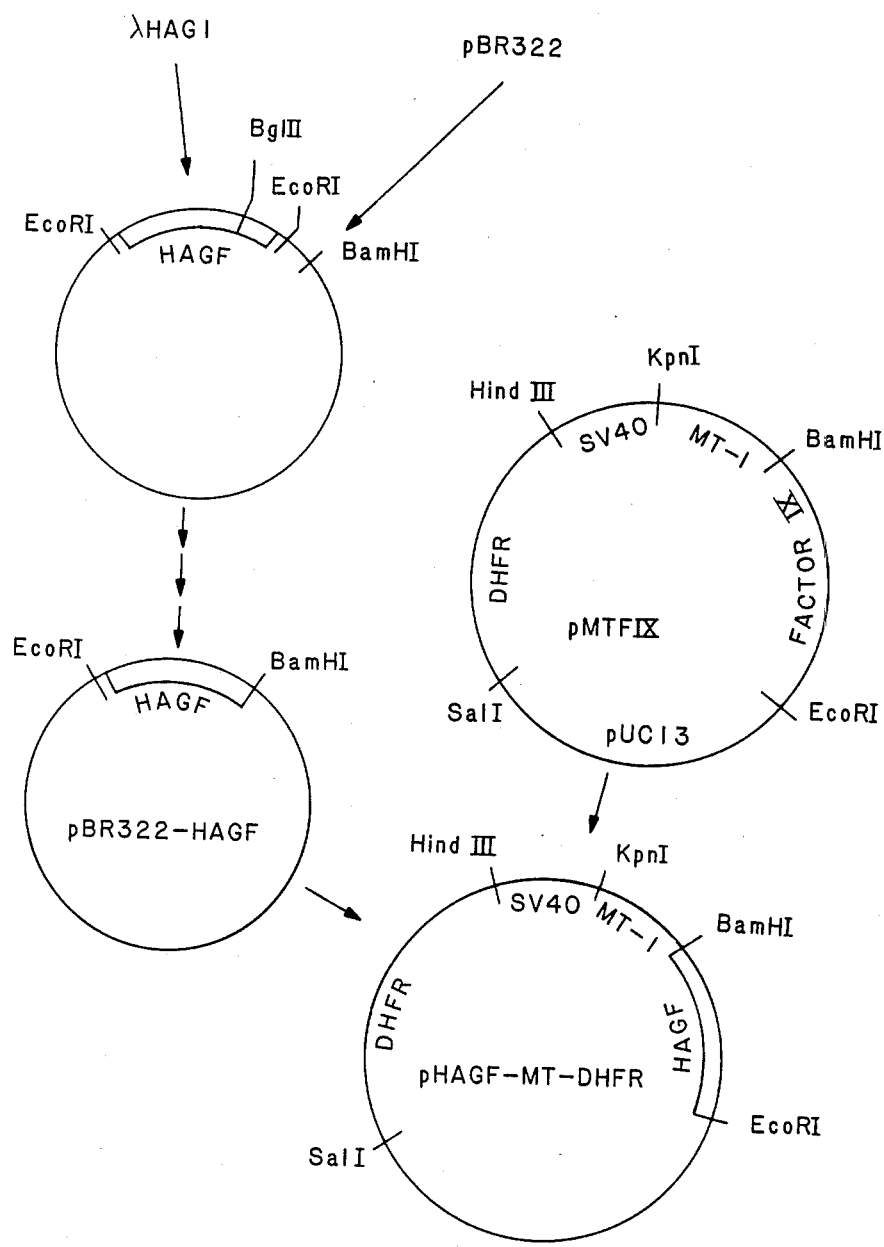
FIG. 4 illustrates the construction of the mammalian cell expression vector pHAGF-MT-DHFR.

As shown in FIG. 4, the HAGF insert was isolated from $\lambda$HAG1 as a PvuII fragment and inserted into pBR322 which had been linearized with SmaI. The resultant plasmid was then digested with BglII, which cuts in the 5' untranslated region of the HAGF sequence. The DNA was then digested with Bal 31 to produce a HAGF sequence having a 5' terminus at nucleotide +7 from the site of transcription initiation. The DNA was then digested with BamHI. The resulting fragment ends were blunted using DNA polymerase I (Klenow fragment) and the fragment comprising the pBR322 and HAGF coding sequences was purified by electrophoresis on a 0.7% agarose gel. The DNA was extracted from the gel and recircularized. The resultant plasmid, designated pBR322-HAGF, was digested with BamHI and EcoRI and the ~3 kb fragment comprising the angiogenin sequence was purified by electrophoresis on a 0.7% agarose gel.

The final expression vector was then constructed in the following manner. Plasmid pMTFIX (Kurachi and Palmiter, *Thrombosis and Hemostasis* 54: 282, 1985), comprising the mouse metallothionein (MT-1) promoter, human Factor IX coding sequence, SV40 promoter, and a modified DHFR gene (Levinson et al., EPO publication 117,060) was digested with BamHI and EcoRI (FIG. 4). The fragment comprising the pUC13 sequence and the SV40-DHFR expression unit was gel purified. This segment was then joined to the BamHI-EcoRI HAGF fragment. The resultant vector was designated pHAGF-MT-DHFR (FIG. 4).

Plasmid pHAGF-MT-DHFR was then transferred into baby hamster kidney (BHK) cells by standard calcium phosphate-mediated transfection procedures. Cells containing the vector were grown at 37° C. in 5% $CO_2$ in Dulbecco's modified Eagle's medium containing glucose and glutamine (Gibco), supplemented with 3.7 g/l $NaHCO_3$, 10% heat inactivated fetal calf serum and antibiotics. Cells containing the plasmid were then selected for methotrexate (MTX) resistance by sequentially increasing the concentration of MTX in the culture medium. MTX concentrations used were 1 $\mu$M, 10 $\mu$M, 100 $\mu$M, and 1 mM. Cells which survived in the presence of 1 mM MTX were then induced by the addition of either 80 $\mu$M $ZnSO_4$, 2 $\mu$M $CdSO_4$, or a mixture of the two salts to the culture medium.

Angiogenin mRNA was assayed essentially as described by Durnam and Palmiter (*Analyt. Biochem.* 131: 385–393, 1983). Sense strand DNA from an M13mp18 clone containing the entire angiogenin gene in a ~2.9 kb insert was used to make a standard curve. A dodecaoligonucleotide complementary to the coding sequence for amino acids 35 to 41 of angiogenin was labelled with $^{32}P$ at its 5' end and used as a probe in solution hybridization.

Messenger RNA levels were elevated >20-fold using $Cd^{++}$ induction and >15-fold for $Zn^{++}$ induction.

To assay for the presence of angiogenin, the induced, conditioned medium was acidified, frozen and thawed, centrifuged, and the supernatant dialyzed against water and lyophilized. The lyophilized material was then dissolved in and dialyzed against 0.1M sodium phosphate buffer pH 6.6, supplemented with lysozyme as a carrier. The dialyzed sample was applied to a column of CM-52 cellulose and partially purified angiogenin was eluted with the same buffer containing 1M NaCl. The eluate was applied to a C18 reversed phase HPLC column and fractionated as described above. A protein having the chromatographic and electrophoretic properties of tumor-derived angiogenin was obtained.

The resultant protein is assayed for angiogenic activity by the CAM method using published procedures.

EXAMPLE 3

Production of Angiogenin in Yeast

Figure 6:
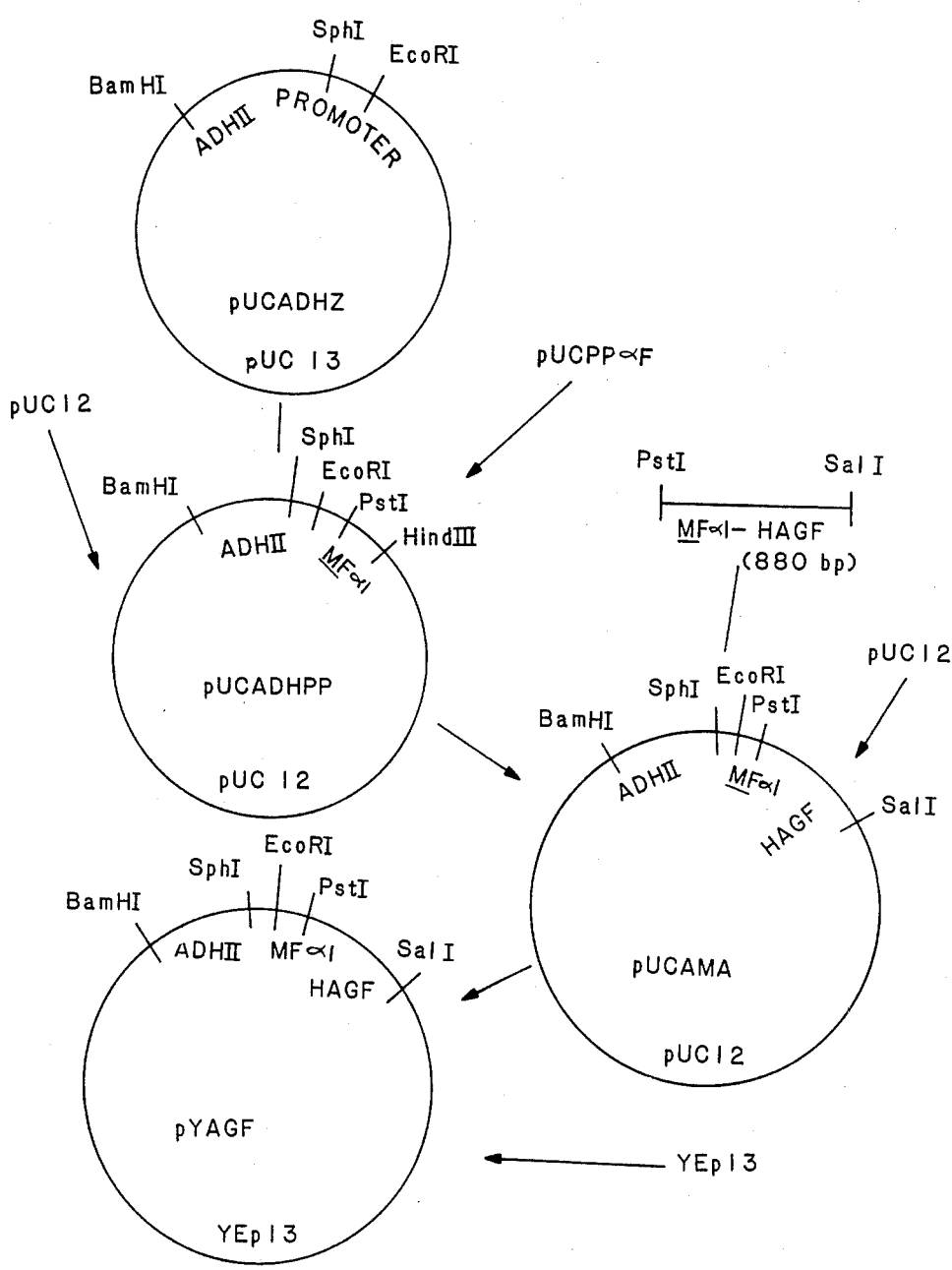

A vector for expressing angiogenin in transformed yeast is illustrated in FIG. 6. It contains an expression unit consisting of the yeast ADHII promoter (Young et al., in *Genetic Engineering of Microorganisms for Chemicals*, Hollaender et al., eds., p. 335, Plenum, New York, 1982), a portion of the MF α1 pre-pro sequence (Kurjan and Herskowitz, *Cell* 30: 933–943, 1982), and the HAGF sequence.

A portion of the ADHII gene is obtained from the plasmid pADR2 (Beier and Young, *Nature* 300: 724–728, 1982) as a SphI fragment of approximately 1530 bp. This fragment is subcloned into an M13 phage vector and mutagenized essentially as described by Zoller et al. (*Manual for Advanced Techniques in Molecular Cloning Course*, Cold Spring Harbor Laboratory, 1983) using a mutagenic primer having the sequence GTA ATA CAC AGA ATT CAT TCC AGA AA. The replicative form of the mutagenized phage is digested with SphI and Eco RI and a partial ADH II promoter fragment of approximately 176 bp is purified. The upstream portion of the promoter is then restored by joining the ~176 bp fragment, the ~1 kb Bam HI-SphI fragment of ADH II (from pADR2), and Bam HI+Eco RI cut pUC13. The resultant plasmid is designated pUCADH2 (FIG. 6).

Figure 5:
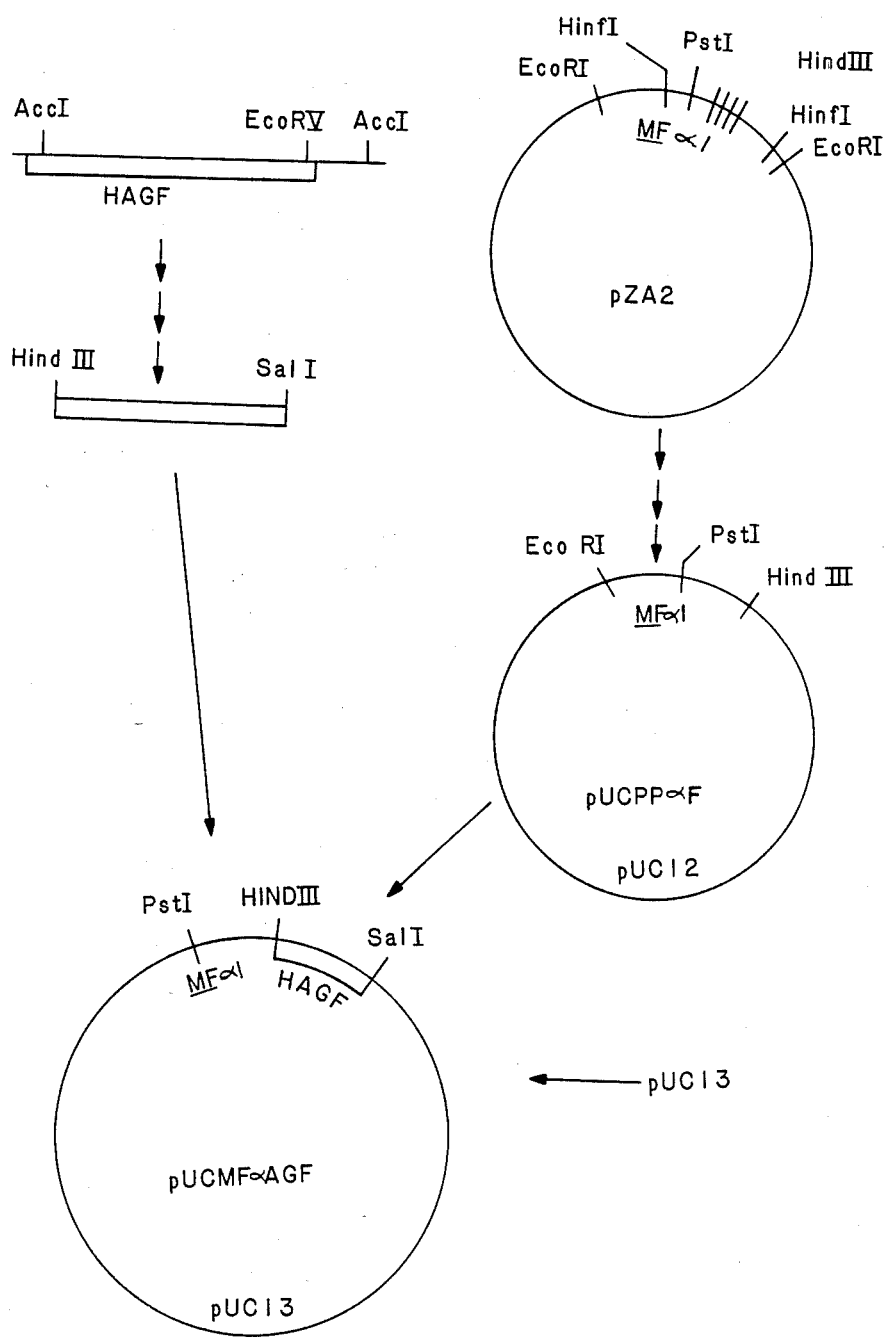
FIGS. 5 and 6 illustrate the construction of the yeast expression vector pYAGF.

Referring to FIG. 5, the MFα1 gene is obtained from a yeast genomic library of partial Sau 3A fragments cloned into the Bam HI site of YEp13 (Nasmyth and Tatchell, *Cell* 19: 753–764, 1980) and identified by complementation of the matα2 mutation. One such clone is designated pZA2. The MFα1 sequence is cut at position −71 with HinfI, the ends filled using DNA polymerase I (Klenow fragment), and Eco RI linkers are added. The signal sequence is then isolated as an Eco RI-Hind III fragment and subcloned in pUC12 to construct plasmid pUCPPαF.

The HAGF coding sequence is isolated from λHAG1 as a 1115 bp AccI fragment. The fragment ends are blunted using DNA polymerase I (Klenow fragment) and Hind III linkers are added to the ends. The resultant fragment is digested with Hind III and Eco RV and a ~666 bp fragment is gel purified. Sal I linkers are then ligated to the Eco RV terminus, the fragment is cut with Sal I, and the ~674 bp fragment is gel purified.

The HAGF sequence is then joined to a portion of the MFα1 signal sequence. Plasmid pUCPPαF is digested with PstI and Hind III and the 237 bp fragment is isolated. The ~674 bp HAGF fragment and the 237 bp MFα1 fragment are ligated to Pst I+Sal I cut pUC13. The resultant recombinant plasmid is digested with Pst I and Sal I and the ~911 bp MFα1-HAGF fragment is gel purified and inserted into Pst I+Sal I cut M13mp10 (replicative form). A precise junction between the Lys-Arg processing site of MFα1 and the first amino acid of angiogenin is achieved through in vitro mutagenesis of the resultant recombinant phage using the mutagenic primer TGG ATA AAA GAC AGG ATA ACTC. The replicative form of the mutagenized phage is cut with Pst I and Sal I and the ~880 bp MFα1-HAGF fragment is gel purified.

Referring to FIG. 6, the ADH II-MFα1-HAGF expression unit is then assembled. Plasmid pUCADH2 is cut with Bam HI and Eco RI an the ~1200 bp ADH II fragment is gel purified. Plasmid pUCPPαF is cut with Eco RI and Hind III and the ~340 bp MFα1 fragment is gel purified. The two fragments are ligated to Bam HI+Hind III cut pUC12 to construct pUCADHPP. This plasmid is digested with Bam HI and Pst I and the ~1300 bp ADHII-MFα1 fragment is purified. This fragment and the ~880 bp MFα1-HAGF fragment are then joined, in a triple ligation, to Bam HI+Sal I cut pUC12. The resultant plasmid is designated pUCAMA.

The yeast expression vector pYAGF is constructed by ligating the Bam HI-Hind III expression unit fragment from pUCAMA to Bam HI+Hind III digested YEp13.

Yeast cells are transformed with pYAGF and cultured by conventional methods. Angiogenin is purified from cell extracts or culture media essentially as described above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A plasmid identical to ATCC Deposit No. 40192.

2. A purified isolated DNA sequence consisting essentially of a DNA sequence coding for the protein defined in FIG. 1 or for a protein having substantially the same amino acid sequence and substantially the same angiogenic activity as the protein defined in FIG. 1.

3. A plasmid identical to ATCC Deposit No. 40193.

4. An isolated vector for expressing in transformed yeast the protein defined in FIG. 1 or a protein having substantially the same amino acid sequence and substantially the same angiogenic activity as the protein of FIG. 1, which vector includes a DNA construct comprising the DNA sequence claimed in claim 2, a promoter upstream of and operably linked to said sequence, and a polyadenylation signal downstream thereof.

5. A vector as claimed in claim 4 in which said promoter is the yeast ADHII promoter.

6. An isolated vector for expressing in a transformed mammalian cell the protein defined in FIG. 1 or a protein having substantially the same amino acid sequence and substantially the same angiogenic activity as the protein of FIG. 1, which vector includes a DNA construct comprising the DNA sequence claimed in claim 2, a promoter upstream of and operably linked to said sequence, and a polyadenylation signal downstream thereof.

7. A vector as claimed in claim 6 in which said promoter is the mouse metallothionein-1 promoter.

8. A yeast cell containing the DNA sequence coding for the protein defined in FIG. 1 or a protein having substantially the same amino acid sequence and substantially the same angiogenic activity as the protein of FIG. 1, a promoter upstream of and operably linked to said sequence, and a polyadenylation signal downstream thereof.

9. A method for producing the protein defined in FIG. 1 or a protein having substantially the same amino acid sequence and substantially the same angiogenic activity as the protein of FIG. 1, comprising the steps of inserting into cells a DNA vector having a construct comprising the DNA sequence claimed in claim 2, a promoter upstream of and operably linked to said sequence, and a polyadenylation signal downstream thereof, growing said cells in a suitable medium, and separating said protein from said cells.

10. A method as claimed in claim 9 wherein said cell is a yeast cell.

11. A method as claimed in claim 9 wherein said cell is a mammalian cell.

12. A method as claimed in claim 9 wherein said cell is a bacterial cell.

* * * * *

UNITED STATES PATENT AND TRADEMARK OFFICE
CERTIFICATE OF CORRECTION

PATENT NO. : 4,721,672
DATED : January 26, 1988
INVENTOR(S) : Bert L. Vallee et al It is certified that error appears in the above-identified patent and that said Letters Patent is hereby corrected as shown below:

On the title page of the patent "Appl. No. 798,547" should be --Appl. No. 778,547 --.

Under "OTHER PUBLICATIONS", Kumer et al" should be -- Kumar et al --.

In the "Abstract", line 7, "diagnostic" is misspelled;

Column 4, line 36, "of acidification" should be -- is acidification --;

Column 7, line 38, "angiogenin" is misspelled;

Column 7, line 40, "and histidines" should be --the histidines --,

Signed and Sealed this

Second Day of August, 1988

Attest:

DONALD J. QUIGG

*Attesting Officer*  *Commissioner of Patents and Trademarks*